(12) United States Patent
Melnichuk et al.

(10) Patent No.: US 10,625,176 B2
(45) Date of Patent: Apr. 21, 2020

(54) METHOD FOR CONTINUOUS EXTRACTION AND SEPARATION OF USEFUL COMPOUNDS FOR PLANT OR ANIMAL MATERIAL

(71) Applicants: Larry Jack Melnichuk, Burlington (CA); Karen Sue Kelly, Burlington (CA)

(72) Inventors: Larry Jack Melnichuk, Burlington (CA); Karen Sue Kelly, Burlington (CA)

( * ) Notice: Subject to any disclaimer, the term of this patent is extended or adjusted under 35 U.S.C. 154(b) by 0 days.

(21) Appl. No.: 15/947,013

(22) Filed: Apr. 6, 2018

(65) Prior Publication Data

US 2020/0023286 A1    Jan. 23, 2020

(51) Int. Cl.
*C07D 401/04* (2006.01)
*B01D 11/02* (2006.01)
*C07C 45/80* (2006.01)

(52) U.S. Cl.
CPC ...... *B01D 11/0288* (2013.01); *B01D 11/0296* (2013.01); *C07C 45/80* (2013.01); *C07D 401/04* (2013.01)

(58) Field of Classification Search
CPC ............ B01D 11/0288; B01D 11/0296; C07D 401/04; C07C 45/80
USPC ................................................ 546/518, 279.4
See application file for complete search history.

(56) References Cited

U.S. PATENT DOCUMENTS

| | | | |
|---|---|---|---|
| 6,403,126 B1* | 6/2002 | Webster | A61K 36/185 424/725 |
| 8,048,304 B2* | 11/2011 | Waibel | B01D 11/0203 210/634 |
| 9,358,259 B2* | 6/2016 | Hospodor | A61K 36/185 |
| 9,399,180 B2* | 7/2016 | Ellis | B01D 11/0207 |
| 9,669,328 B2* | 6/2017 | Jones | C11B 1/10 |
| 9,782,691 B2* | 10/2017 | Chess | B01D 11/0203 |
| 9,789,147 B2* | 10/2017 | Jones | B01D 11/0219 |
| 9,844,740 B2* | 12/2017 | Jones | C11B 1/10 |

\* cited by examiner

*Primary Examiner* — Taylor V Oh

(57) ABSTRACT

This invention describes a method to extract and separate compounds from plant or animal material in a continuous process. The method uses dimethyl ether as a safe and efficient solvent which will extract polar and non-polar compounds. The extracted compounds are separated by distillation which is configured to provide individual compounds or groups of compounds.

19 Claims, 1 Drawing Sheet

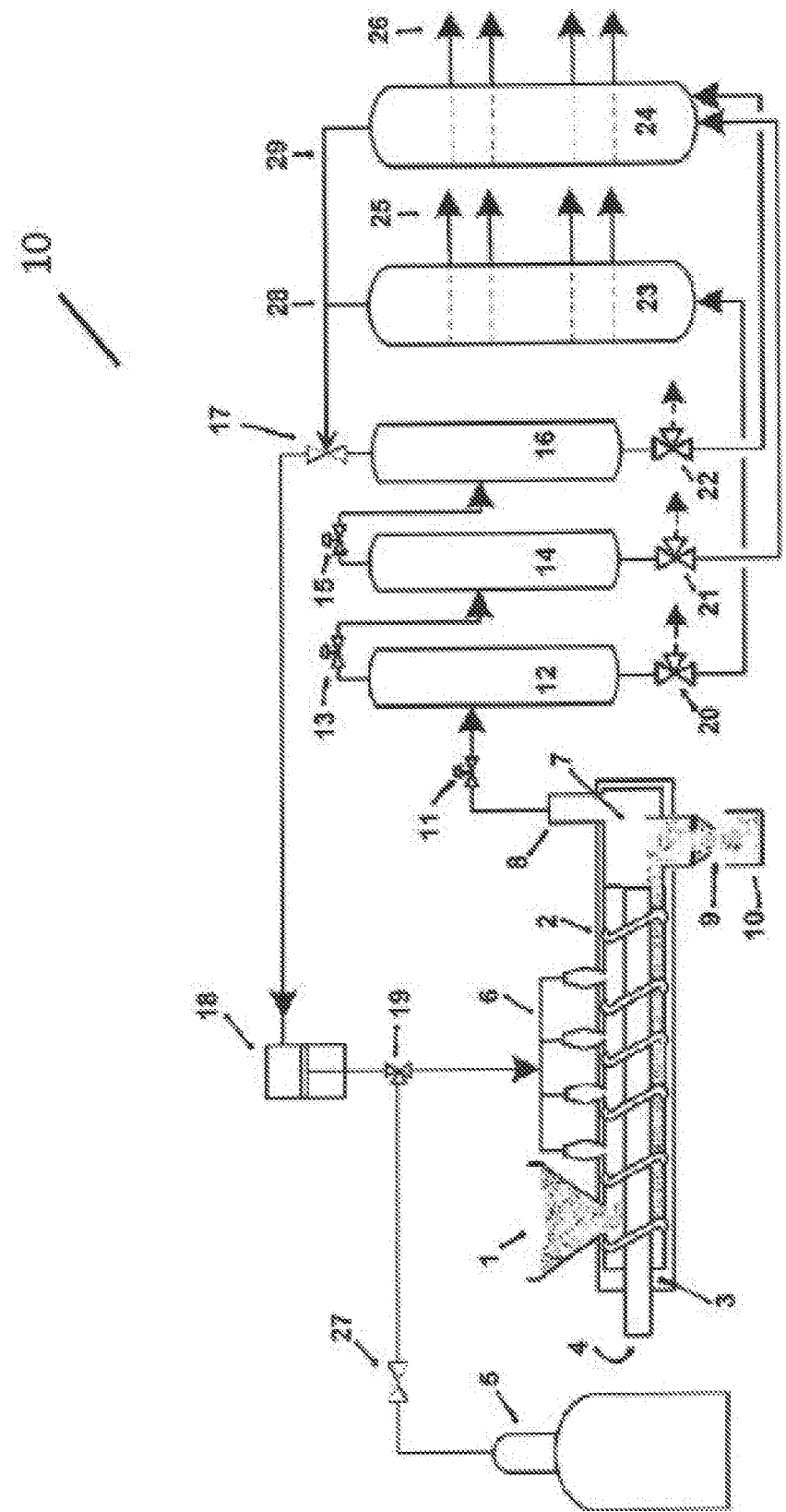

METHOD FOR CONTINUOUS EXTRACTION AND SEPARATION OF USEFUL COMPOUNDS FOR PLANT OR ANIMAL MATERIAL

FIELD OF THE INVENTION

Disclosed herein is a continuous, scalable method to obtain isolates or groups of isolates by the extraction of compounds from plant or animal material using dimethyl ether and the purification of the said isolates using distillation.

BACKGROUND OF THE INVENTION

The importance of the process of extraction has increased with the growing global awareness of the medical and nutritional benefits of plant and animal isolates. For example, fish oils are extracted to provide healthy fatty acids, fats are separated from milk to reduce its fat content, and flavors, spices and herbal isolates are extracted from plants. In general, these extraction methods are specific for one or two solutes present in the material. Most continuous extraction methods are not chemical in nature, but are mechanical, such as the extraction of seed oils. As such, extraction methods are not complex, and do not provide for the separation of the final solutes.

In the example of *cannabis* species it has been discovered that compounds within it provide medicinal benefit for such conditions as inflammation, pain, nausea and epilepsy. Until recently, the belief in the "Entourage Effect" meant that the use of a totality of the plant in some way, such as smoking or consuming whole extracts, was necessary to achieve the effects. This has been disproven—for example, the drugs Marinol and Syndros include the active ingredient dronabinol, a synthetic delta-9-tetrahydrocannabinol (THC). Cesamet includes the active ingredient nabilone, which is synthetically derived and has a chemical structure similar to THC.

There are some 60 possible bio-active compounds within the *cannabis* plant. Some of these compounds are predicted to be valuable natural-source drugs which may not be associated with the plethora of side effects which plague commercial synthetic drugs.

Recently there has evolved methods and solvents used to extract products from *cannabis* species. Originally, leaves, stems and buds from the plants were dried and smoked. Awareness that solvent extraction could be used to obtain an edible oil product which had similar effects, without the detrimental effects of smoking, led to experimentation with solvents. As more exploration of *cannabis* took place, it was recognized that there are a plethora of active ingredients in the *cannabis* buds. It has been long thought that to get the benefit of *cannabis*, the consumption or smoking of all of its compounds was necessary, resulting in what has been termed the Entourage Effect.

Early extraction used naphtha, ethyl ether, butane, 99% isopropyl alcohol, or hexane. When *cannabis* use increased, commercial equipment was marketed. Subsequent extractors used propane or butane, or a mixture of both, to extract the *cannabis* oils. Post-extraction treatment of the oils, such as cooling or heating, or adding ethanol to the oil, produced quirky physical forms of the extracts, such as shatter, wax, errl, oil, live resin, or dabs. However, there is always the propensity for some residue of the solvent used in the extraction process remaining in the end product. In the case of ethanol, this may not be toxic, but it is nevertheless undesirable.

As legalization occurred, *cannabis* use also has increased, and more effort has been made to regulate the quality of the *cannabis* products. For example, solvent, fertilizer and herbicide residues have been restricted. The difficulty of obtaining a residue-free product was the impetus for further development of the extraction process. The use of supercritical fluids was found to be an alternative technique that produces extracts with none or fewer polar impurities than the conventional organic liquid extracts. It is considered to be a green technology, since a concentration step is most often eliminated after the extraction process.

For any solvent, its vapor/liquid equilibrium curve culminates at the critical point (CP), above which only one phase occurs. All solvents possess a CP, which is characterized by a critical temperature ($T_c$) and a critical pressure ($P_c$). Experimental studies using SFE are usually limited to the region of $P_c < P \leq 6P_c$ and $T_c < T \leq 1.4T_c$.

The most commonly used supercritical fluid is $CO_2$ because it has favorable $T_c$ and $P_c$ (31.1° C. and 73.9 bar) that are ideal for the extraction of thermolabile compounds. In addition, supercritical $CO_2$ has low viscosity, low surface tension, high diffusivity and good density and is also non-toxic, non-flammable, cheap, widely available, chemically inert under several conditions, and gaseous at normal pressure and temperature, eliminating the step of solvent evaporation after extraction. Furthermore, $CO_2$ gives a non-oxidizing atmosphere in extractions, thus preventing extracts from degradation.

The greatest limitation of supercritical $CO_2$ is that it is not suitable to extract polar compounds. It is necessary to add an organic modifier or entrainer, such as ethanol or methanol to greatly improve extraction efficiency. The use of methanol may result in unacceptable residues in the product.

Other solvents, such as water, methanol, ethanol, acetone, chloroform, ethyl acetate, and toluene, are not appropriate to extract bioactive compounds, because their $T_c$ is above 200° C.

BRIEF SUMMARY OF THE INVENTION

What is lacking in the extraction industry is a scalable method of continuously extracting compounds from material using a non-residual solvent and further processing the extract to separate and isolate compounds for further use. The instant invention provides a method in which a safe extract can be obtained which contains virtually all of the important compounds present in the material and further provides a method of their subsequent separation for further use as individual compounds or as blended groups. This separation thus provides a myriad of possible therapeutic, targeted, compounds which may well prove to be of significant medical benefit, both in animals and in humans.

The invention herein describes a continuous process and solvent which offer significant improvements and advantages over supercritical extractions such as carbon dioxide or water. The solvent used in the invention herein is dimethyl ether ("DME"). DME is the simplest ether, and is non-anaesthetizing. DME is a gas above −24° C., and in the instant invention is used in liquid form. DME is a very useful solvent because it readily dissolves oils and similar compounds. DME also dehydrates, and is partially soluble in water. It therefore extracts water-based compounds. It readily vaporizes and leaves no residue. DME breaks down in the environment into carbon dioxide and water and is not toxic. DME is also relatively safe, and requires no more handling precautions than the use of propane.

Since DME is partially miscible with water, it allows the simultaneous extraction of non-polar target compounds and the removal of water from wet matrices. Moreover, the liquefied DME (with $T_c=127°$ C. and $P_c=53.7$ bar) is evaporated under low-pressure conditions and taken off as a gas, since its normal boiling point is low ($-24.8°$ C.) and its saturated vapor pressure at 20° C. is 5.1 bar. An advantage of DME over other ethers is that it is resistant to autoxidation.

In the instant invention, liquid DME is mixed with the material to be extracted. The pressure is initially maintained such that the DME remains a liquid while thoroughly mixing with the material. Once saturated, the pressure is reduced to allow the DME to vaporize, carrying with it the dissolved solutes. In a subsequent series of vessels, which number depends on the characteristics of the solutes, the solutes are condensed. At the end of this condensation sequence, the DME is removed for discharge or recycle.

The condensed extracted solutes are then sent to be distilled. The distillation columns are configured with the appropriate temperature and number of trays such that the solutes are isolated and collected. The distillation can be accomplished in one or more towers, which gives the instant invention flexibility and can be used for a multitude of extracted solutes. The isolated compounds can then be collected and either used as is or recombined as groups.

BRIEF DESCRIPTION OF DRAWINGS

FIG. 1 This FIGURE shows an embodiment of the process using plant material, in this case *cannabis* sp., in which material is fed into the extraction device, the solutes collected and sent to the distillation apparatus.

DESCRIPTION OF THE INVENTION

The following description is one embodiment of the invention. The instant invention could be embodied in other equipment configurations, but the main features are that the process utilizes DME as a solvent to extract solutes from material, which are then distilled to provide either single compounds or groups thereof.

A person skilled in the art would recognize readily be able to configure a method to prepare the input material for use in the instant process. Similarly, the skilled person would be able to identify the solutes which are important to separate from the extraction, and configure the distillation column(s) appropriately.

Example 1

In this embodiment, *cannabis* is used as the material. There are different ways to prepare the *cannabis* for extraction. Typically buds of the female plant contain the highest quantities of cannabinoids, and therefore the invention is very effective for their use. The preparation could consist of grinding or milling the buds in some way, to render them in small particles with optimized surface area. Experiments have also been done using ultrasound on ground *cannabis* buds, with the resulting material providing increased extraction yields because of increased surface area for solvent exposure. Whichever method is used to prepare the buds, the final material will lend itself to balancing the perfusion of the DME amongst the material to extract the maximum cannabinoid mass.

It is understood that those skilled in the art might find improvements to the methods described in these embodiments, which are meant to teach the principles involved in the physical saturation of the material with the DME, the extraction conditions, the collection of the extractant and DME mixture, the removal of the spent material, the subsequent separation of the extractant from the DME, and lastly, the optional step or steps of isolating one or more of the products of the extraction.

One embodiment of the present invention used to extract and separate products from *cannabis* species is described at FIG. 1 at 10. This is not necessarily the preferred embodiment, but is shown to demonstrate the features of the invention in such a way to illuminate its goals, and to provide possible opportunities for those skilled in the art to modify the equipment in such a way as to maximize the composition and selection of the end products of the invention.

Feedstock comprised of the prepared *cannabis* plant material from which the extraction is to be performed is fed at 1 into a vessel 2. The plant material is prepared according to the feed method used. For example, the plant material can be fed using a surge bin, a metered hopper, or an auger or other device. If the device is to be used in a continuous fashion, the feed system will be configured to provide a constant volume of the prepared feedstock. In that regard, the feed method will require a reservoir of some type or in itself be a continuously fed device.

The vessel 2 is built to withstand pressures above 5 atmospheres. The vessel is surrounded by a heating jacket 3, which heat may be provided by water or electrical power. Heat from the jacket may be used to increase the solvent action of the DME and ensure total saturation. The plant material enters the vessel, which surrounds a motorized feed screw 4 with wide blades filling the interior of the vessel. The blades of the feed screw provide a seal against the interior vessel wall and are configured such that they provide agitation to the input material.

Liquid dimethyl ether ("DME") is supplied from a canister 5 controlled by a valve 27 and fed into the vessel through flush nozzles 6 which are located in the upper surface of the vessel. A plurality of nozzles ensure the thorough saturation of the plant material with the liquid DME. The quantity of input *cannabis* material must be taken into account when controlling the flow of DME through the reactor vessel, to ensure complete extraction. The pressure of the injected liquid DME pressurizes the immediate compartment of the feed screw into which the DME is injected. As the plant material tumbles around in the liquid DME from the agitation caused by the action of the feed screw, it becomes thoroughly mixed with the DME. While this is happening, the pressure is gradually dissipating as the feed screw turns and the material is pushed towards the end of the vessel. The volume of liquid DME supplied is adjusted to the volume of the plant material present, and is sufficient to dissolve and extract the burden of cannabinoids, terpenes and flavones present in the material. The heat is adjusted in the heating jacket to ensure complete extraction. The rate of the feed screw is set to provide the maximum effect of thoroughly mixing the DME with the plant material. The goal of this part of the process is to ensure full mixing of the DME with the material and allowing contact for sufficient time as to extract virtually all of the possible compounds.

The plant material progresses in the feed screw to the end of the apparatus, where it enters a collection portion 7 of the surrounding vessel. At this point, the pressure initially created by the liquid DME has somewhat dissipated and the pressure inside the chamber is maintained at a range which is above atmospheric but lower than 5 atmospheres. The pressure in the collection area 7 of the vessel allows the DME to return to its vapor state, and carry with it all dissolved solutes. The vapors of DME, containing the dissolved cannabinoids, terpenes and flavones, exit through a port 8 located in the top of the vessel. The exiting port 8 is fitted with a check valve, allowing vapors to escape while maintaining the pressure inside the compartment.

The spent plant material collects at the bottom of the collection area 5, the weight of which triggers an automatic door system 9 from time to time, causing the spent plant material to fall into a collection vessel 10, below the exit port 9.

Vapors exiting the vessel at 8 containing dissolved cannabinoids, terpenes and flavonoids are sent to a first pressure-reducing valve 11 where the pressure is reduced to between 4 and 3 atmospheres, and enter a first collection vessel 12. The heavy oils and waxes condense from the vapor and are deposited in the vessel. The DME vapors, still carrying other compounds, exit the vessel 12 and pass through a second pressure-reducing valve 13 further reducing the pressure to between 3 and 2 atmospheres, and are directed into a second vessel 14. The pressure in vessel 14 is low enough to cause the medium-weight cannabinoids to condense and collect. The vaporous DME, still bearing some compounds, exits vessel 14 and pass through a third pressure-reducing valve 15, where the pressure is reduced to atmospheric. The gases pass into a third vessel 16, where the lowest weight compounds, terpenes and flavonoids, condense and collect.

The DME, now devoid of solutes, exits vessel 16 and enters a recycle loop, passing though a check/mixing valve at 17 and enter a compressor 18. The compressor recompresses the DME to at least 5 atmospheres, when it then becomes liquid. The DME enters a mixing valve 19 where it merges with fresh DME from tank 3, to provide solvent for the process.

The collected liquid heavy oils and waxes in vessel 12 exit the bottom of the vessel and flow into a valve 20, which reduces the pressure to atmospheric. The liquids progress to the first distillation tower 23. This distillation column is designed to separate any of the desired compounds from the liquids. Similarly, the liquid cannabinoids in vessel 14 exit the bottom and flow through a valve 21 which reduces the pressure to one atmosphere. These liquids enter a second distillation tower 24. Similarly, the liquid terpenes and flavonoids exit the vessel 16 and pass through valve 22 before entering the second distillation column 24. In the instant embodiment, the outputs of distillation columns 23 and 24 are shown as multiple streams 25 and 26 which are representation of the various output products. Each distillation column 23 and 24 are fitted with exit ports 28 and 29 at the top of each column. Any residual DME either not previously volatized from the solutes will be in vapor form. DME exiting from the columns are sent to the check/mixing valve 17 to be recycled.

Optionally, the contents of each collection vessel 12, 14 and 16 may be collected without further distillation, shown at 20, 21 and 22. It is understood that although at the current time, there does not appear to be a use for the waxes and heavy oils which are collected in vessel 12, in the future these products may provide to have purpose or therapeutic value. The instant invention provides a method by which these may also be collected and isolated.

It is understood that the distillation columns can be optionally configured to the user's choice of separating out single products, or blends of products. The flexibility allows users to extract from as few or as many of the many compounds present in *cannabis*. Distillation columns may be added to further separate out individual compounds.

The described embodiment is one option for implementation of the instant invention. Other equipment configurations may accomplish the same extraction, providing that the basic tenants of the invention are met. It is important to keep the DME in liquid phase while exposing it to the plant material. A contact time is not specified because it would vary with the method used to expose the material to the solvent and can be adjusted. Other methods such as a vibrating bed, under pressure, may accomplish optimum solvent action of the DME with the plant material. The food processing industry is rife with many devices which successfully extract compounds such as terpenes and flavonoids from botanical material. These methods may be adapted to be used under pressure, or be cold enough to liquefy the DME. DME condenses at $-24°$ C., and methods which chill the extraction vessel would be equally effective. A limitation in that case may be that the media from which extraction is desired would be finely rendered to break up any water which has frozen. Once the liquid DME is saturated with the solutes, then warming to the DME boiling point (above $-24°$ C.) would accomplish the successful vaporization of the DME, leaving the desired solutes behind.

Once the DME has dissolved the desired solutes, and been removed from them, the separation of the various compounds may be done by either distillation, as in the described embodiment, molecular sieves or modified centrifugation should they be available. Alternate methods of separation may be available through modifications of cryogenic methods. These methods may be expensive, and not produce the separation of the compounds which is available through distillation. The technology of separation via the use of molecular sieves when the compounds are in the vapor phase is not yet developed to accommodate large molecules.

An person skilled in the art will be able to successfully achieve the instant invention through use of modern industrial construction techniques. There is no new equipment in the instant process described. The entire process can be mechanized and controlled using proper computerized control points such as thermocouples and pressure sensors to enable automated process control. The location and programming of these sensors is not elucidated here. In addition, pumps and motors can be supplied to various pieces of equipment to enable smooth, continuous operation. The timing and regulation of all steps in the instant process are well with technological reach.

INDUSTRIAL APPLICABILITY

The instant invention has particular use in the *cannabis* industry. As the industry is evolving and new knowledge is coming to light, it is evident that there are many compounds in *cannabis* which need to be isolated and explored for their medicinal value. The instant invention provides the ability to isolate those compounds using a solvent which is without residues. The process is continuous and therefore has commercial use for extracting significant volumes of the compound. The advantages of the instant process over the current commercial processes are: the instant process is continuous; the instant invention uses a safe, lower-pressure solvent with no residues; and the instant invention separates *cannabis* compounds so they can then be tested or used individually.

The instant invention could be used to extract solutes from lipid-bearing material such as *Euphausia superba* (krill), which is typically done using acetone. There are three major desirable commercial products in krill: omega 3 fatty acids, phospholipids, and astaxanthin. The acetone extraction is dangerous and is difficult to cleanse of residues. Using the instant invention in this extraction would be an efficient and safe improvement.

The instant invention would also be very useful for the extraction of nicotine from the tobacco plant. Anyone skilled in the art would easily apply the principles herein to the creation of an efficient process, which would not differ greatly from the described embodiment. The number of collection vessels and distillation columns may be reduced. The dissolved nicotine would condense out in the collection vessel(s), and the distillation column(s) may be able to be combined into one. The resulting pure liquid nicotine would be suitable for production of a vaping product for market.

Disclosures

The use of dimethyl ether (DME) has not been used on a commercial scale for *cannabis* extractions which are suitable for further processing to separate or isolate either groups or specific compounds. It has been used in lipid extractions, but again the products are used as extracted with no attempts at further processing or separation. The following disclosures are related to extraction but all of them lack at least one of the instant invention main features of continuous feed, non-residual DME solvent, or separation of products.

NON-PATENT LITERATURE

An available home *cannabis* extraction is performed at room temperatures. The DME is sold in a standard 100-300 ml pressurized canister, under pressures around 5.1-5.9 bar, under the trade name of SoDoDex. The DME canister is inverted over a metal cylinder loosely packed with ground or finely divided plant material, a metal sieve plate separating the insertion point of the DME to prevent the plant material overflowing. The DME is released from the can and allowed to drip through the plant material. The liquid is filtered at the end of the cylinder and drips into a collection pan. DME then evaporates from the extract in the open extraction pan. The DME leaves no residue. The extracted liquid slowly thickens as the DME evaporates. This is the only known DME extraction device, and operates at atmospheric pressure with no separation of the product. This device lacks continuous feed and product separation.

PATENT LITERATURE

U.S. Pat. No. 6,403,126 (Webster et al) discloses a method of extracting in which petroleum derived hydrocarbon; toluene; trimethylpentane, a low molecular weight alcohol; ethanol; a low molecular weight chlorinated hydrocarbon; and dichloromethane various products from hemp, lacking $\Delta^9$-THC is conducted via column chromatography. This methods lacks continuous feed, DME, and is limited to very small quantities.

U.S. Pat. No. 9,782,691 (Chess et al) discloses a process in which Super- or Sub-critical $CO_2$ are, alone or with a lower vapor pressure gas or gases, collected and re-used in a closed-loop extraction process. This process lacks dimethyl ether, continuous feed and product separation.

U.S. Pat. No. 9,399,180 (Ellis et al) discloses a vertical extraction process in which liquid gas is applied at the top, a vacuum draws down the extractant, and the gas is removed by cooling and recycled. This product lacks DME, continuous feed and product separation.

U.S. Pat. No. 8,048,304 (Walbel et al) discloses a process for increased efficiency in the recovery and recycle of gases used in an extraction process. This process lacks DME, continuous feed and product separation.

U.S. Pat. No. 9,358,259 (Hospodor et al) discloses a process of extracting cannabinoids in which the solvent is passed through the material many times in a cycle, the extractant remaining behind in a collector tank from which the solvent is removed and recycled. This process lacks DME, continuous feed and product separation.

U.S. Pat. Nos. 9,669,328; 9,789,147; 9,844,740 (Jones) discloses a process of extraction in which extraction takes place using liquid gases after which the product is used as is. The solvent it purified for reuse in some cases. The process relies on gravity for operation. This process lacks DME, continuous feed and product separation.

What is claimed:

1. A process to use dimethyl ether as a solvent to continuously extract soluble compounds from *Plantae* sp. or *Arthropod* sp. material including lipids, terpenes, flavones, cannabinoids and alkaloids and separate them into individual or grouped compounds comprising:
   a. feeding prepared *Plantae* sp. or *Arthropod* sp. material to be extracted into a closed vessel;
   b. saturating said prepared material in the closed vessel with liquid dimethyl ether to form a first mixture;
   c. keeping the first mixture below the boiling point of dimethyl ether by applying sufficient pressure or lowering the temperature such that the dimethyl ether is in liquid phase;
   d. dissolving the soluble compounds including lipids, terpenes, flavones, cannabinoids and alkaloids present in the prepared material into the liquid dimethyl ether to produce a final mixture comprised of the input material and liquid dimethyl ether containing the dissolved soluble compounds including lipids, terpenes, flavones, cannabinoids and alkaloids;
   e. optionally providing heat to the vessel to enable complete the dissolving of the soluble compounds including lipids, terpenes, flavones, cannabinoids and alkaloids into the liquid dimethyl ether;
   f. reducing the pressure of the final mixture causing the dimethyl ether to vaporize with the soluble compounds including lipids, terpenes, flavones, cannabinoids and alkaloids entrained;
   g. allowing the vaporous dimethyl ether carrying the soluble compounds including lipids, terpenes, flavones, cannabinoids and alkaloids to exit from the vessel;
   h. removing the remaining spent input material now devoid of soluble compounds of lipids, terpenes, flavones, cannabinoids and alkaloids from the vessel;
   i. directing the soluble compound-rich dimethyl ether vapor containing lipids, terpenes, flavones, cannabinoids and alkaloids into a series of condensation vessels, each at successively lower pressure;
   j. condensing all of the dissolved soluble compounds including lipids, terpenes, flavones, cannabinoids and alkaloids from the dimethyl ether vapor into the vessels such that all soluble compounds including lipids, terpenes, flavones, cannabinoids and alkaloids are condensed;
   k. removing the pure dimethyl ether from the last vessel;
   l. collecting the condensed soluble compounds including lipids, terpenes, flavones, cannabinoids and alkaloids from each of the vessels and sending all, or any, of them into a distillation column, or any of them to any distillation column;

m. collecting the products of the distillation column or columns separately or collectively.

2. A process according to claim 1 in which the prepared material is *cannabis* sp. and the soluble compounds are at least cannabinoids, terpenes and flavonoids.

3. A process according to claim 1 where the prepared material for extraction is *Euphausia superba* (krill) and at least one of the soluble compounds is astaxanthin.

4. A process according to claim 1 where the prepared material for extraction is *Euphausia superba* (krill) and at least one of the soluble compounds is phospholipid.

5. A process according to claim 1 where the prepared material for extraction is *Nicotiana tabacum* (tobacco) and at least one of the soluble compounds is nicotine.

6. A process according to claim 1 in which the final mixture of dimethyl ether and the prepared material for extraction is initially kept at greater than 5 atmospheres.

7. A process according to claim 1 in which the extraction vessel is kept at a temperature range of 32° F. to 230° F. and a pressure range of 0.5 to 7 atmospheres which together are sufficient to keep the dimethyl ether in liquid phase until the soluble compounds including lipids, terpenes, flavones, cannabinoids and alkaloids extracted from the prepared material and dissolved.

8. A process according to claim 1 in which the dimethyl ether liquid is saturated or partially saturated with the soluble compounds of lipids, terpenes, flavones, cannabinoids and alkaloids extracted from the prepared material to form a final mixture.

9. A process according to claim 1 in which all the soluble compounds including lipids, terpenes, flavones, cannabinoids and alkaloids from the prepared material for extraction are dissolved in the liquid dimethyl ether.

10. A process according to claim 1 in which the heat applied to the final mixture does not exceed the lowest boiling point of the desired extractable soluble compound of one of a lipid, terpene, flavone, cannabinoid or alkaloid contained in the prepared material.

11. A process according to claim 1 where the first condensation vessel condenses and collects any compound with a boiling point above 200° C. from the vaporous dimethyl ether containing the soluble compounds terpenes, flavones, cannabinoids and alkaloids from the final mixture.

12. A process according to claim 1 where the second condensation vessel condenses and collects any compound with a boiling point above 150° C. from the vaporous dimethyl ether containing the soluble compounds lipids, terpenes, flavones, cannabinoids and alkaloids from the final mixture.

13. A process according to claim 1 where the third condensation vessel condenses and collects any compound with a boiling point above 100° C. from the vaporous dimethyl ether containing the soluble compounds lipids, terpenes, flavones, cannabinoids and alkaloids from the final mixture.

14. A process according to claim 1 in which the dimethyl ether is collected from any condensation vessel and compressed for reuse.

15. A process according to claim 1 in which the distillation columns are configured for *Cannabis* sp soluble compounds to isolate at least one cannabinoid.

16. A process according to claim 1 in which the distillation columns are configured for *Cannabis* sp solutes soluble compounds to isolate at least one terpene.

17. A process according to claim 1 in which the distillation columns are configured for *Cannabis* sp soluble compounds to isolate at least one flavonoid.

18. A process according to claim 1 in which the distillation columns are configured for *Euphausia superba* (krill) soluble compounds to isolate at least astaxanthin.

19. A process according to claim 1 in which the distillation columns are configured for *Nicotiana tabacum* (tobacco) soluble compounds to isolate at least the alkaloid nicotine.

* * * * *